(12) United States Patent
Ye et al.

(10) Patent No.: US 8,552,402 B2
(45) Date of Patent: Oct. 8, 2013

(54) SUPER-RESOLUTION MICROSCOPY SYSTEM USING SPECKLE ILLUMINATION AND ARRAY SIGNAL PROCESSING

(75) Inventors: Jong Chul Ye, Daejeon (KR); Jae Duck Jang, Daegu (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 8 days.

(21) Appl. No.: 13/267,051

(22) Filed: Oct. 6, 2011

(65) Prior Publication Data

US 2012/0256101 A1    Oct. 11, 2012

(30) Foreign Application Priority Data

Apr. 8, 2011    (KR) .................. 10-2011-0032783

(51) Int. Cl.
*G01N 21/64*    (2006.01)

(52) U.S. Cl.
USPC ................................................. 250/459.1

(58) Field of Classification Search
USPC .......................................................... 250/459.1
See application file for complete search history.

(56) References Cited

U.S. PATENT DOCUMENTS

| | | | |
|---|---|---|---|
| 2010/0044586 A1* | 2/2010 | Duhr et al. | 250/459.1 |
| 2010/0224796 A1* | 9/2010 | Mertz et al. | 250/459.1 |

OTHER PUBLICATIONS

F. Chiang, "Super-resolution digital speckle photography for micro/nano measurements," 2009, Optics and Lasers in Engineering, vol. 47, pp. 274-279.*
Lee et al., "Simultaneous particle size and concentration measurements using a back-lighted particle imaging system," 2009, Flow Measurement and Instrumentation, vol. 20, pp. 189-199.*
Yin et al., "A fluorescence sectioning endoscopy using dynamic speckle illumination," 2008, SPIE Proceedings, vol. 6851, pp. 68510N-1 to68510N-6.*
Ventalon et al., "Quasi-confocal fluorescence sectioning with dynamic speckle illumination," 2005, Optics Letters, vol. 30, No. 24, pp. 3350-3352.*

* cited by examiner

*Primary Examiner* — Kiho Kim
(74) *Attorney, Agent, or Firm* — Choate, Hall & Stewart LLP; Andrea L. C. Robidoux; Daniel S. Matthews

(57) ABSTRACT

A nano-scale resolution fluorescence microscopy system and a method of obtaining an image using the nano-scale resolution microscopy system, and more particularly, a method and a microscopy system, capable of observing fluorescence probes in high resolution by radiating an irregular diffused light to have an incoherent speckle pattern that has low correlation in an adjacent space are disclosed. According to embodiments of the present invention, a diffraction limit of a fluorescence microscope may be overcome, and a super high resolution image on a nanometer scale may be obtained.

20 Claims, 11 Drawing Sheets

SUPER-RESOLUTION MICROSCOPY SYSTEM USING SPECKLE ILLUMINATION AND ARRAY SIGNAL PROCESSING

CROSS-REFERENCE TO RELATED APPLICATION

This application claims the benefit of Korean Patent Application No. 10-2011-0032783, filed on Apr. 8, 2011, in the Korean Intellectual Property Office, the disclosure of which is incorporated herein by reference.

BACKGROUND

1. Field of the Invention

Embodiments of the present invention relate to a nano-scale resolution microscopy system and methods of obtaining super-resolution images using the nano-scale resolution microscopy system, and more particularly, to methods and microscopy systems, capable of observing specimen at very high resolution by exploiting emission statistics of fluorescence probes excited by speckle illumination.

2. Description of the Related Art

A conventional optical microscope has a fundamental spatial resolution limit dependent on a wavelength of light and the numerical aperture of a lens. The best resolution of a conventional optical microscope corresponds to about a half of a wavelength, which refers to a diffraction limit.

Fluorophores, such as fluorescence probes or fluorescence proteins have been extensively designed to be specific to particular cellular functions such as signal transduction and gene expression, so fluorescence microscopy has become an invaluable tool in biology.

In fluorescence microscopy, fluorophores are directly attached to a region of interest within a cell or particular proteins. However, the conventional microscopes may have a limitation in overcoming the diffraction limit of the microscope optical systems, and more particularly, a limitation in resolving fluorophores which are separately less than the diffraction limit.

To address this problem, super-resolution far-field fluorescence nanoscopy have been extensively investigated. This super-resolution microscopy is to exploit non-linear optical phenomena to break the diffraction limit. In STED microscopy, a Gaussian shape excitation beam and a red-shifted doughnut-shaped STED beam are used to quench excited fluorophores by stimulated emission from excitation to ground state. (Klar, T. A., Jakobs, S., Dyba, M., Egner, A. & Hell, S. W. Fluorescence microscopy with diffraction resolution barrier broken by stimulated emission. *Proceedings of the National Academy of Sciences of the United States of America* 97, 8206-8210 (2000).) In saturated structured illumination microscopy (SSIM), structured illumination is used to extend the spatial bandwidth of the optical system using the synthetic aperture principle. (Gustafsson, M. G. L. Nonlinear structured-illumination microscopy: Wide-field fluorescence imaging with theoretically unlimited resolution. *Proceedings of the National Academy of Sciences of the United States of America* 102, 13081 (2005).) In PALM and STORM for each imaging cycle, an optically resolvable random subset of photoswitchable fluorophores is excited to the active state and then switched off to the dark state quickly using background quenching lights. (Rust, M. J., Bates, M. & Zhuang, X. Sub-diffraction-limit imaging by stochastic optical reconstruction microscopy (STORM). *Nature Methods* 3, 793-796 (2006).)

SUMMARY

An aspect of the present invention provides a nano-scale resolution fluorescence microscopy using dynamic speckle illumination and array signal processing algorithms.

An aspect of the present invention provides a nano-scale resolution fluorescence microscopy system and methods of obtaining super-resolution images using the nano-scale resolution microscopy system, capable of overcoming the diffraction limit of a fluorescence microscope that may be useful for basic and applied scientific researches.

Another aspect of the present invention also provides a nano-scale resolution fluorescence microscopy system and methods of obtaining super resolution images using the nano-scale resolution microscopy system, and sensor array signal processing techniques using any type of fluorophores.

According to an aspect of the present invention, there is provided a nano-scale resolution fluorescence microscopy system, including: a speckle pattern generator to generate dynamic speckle illumination by passing, through a diffuser or spatial light modulator, lights from at least one coherent sources with at least one colors; an incident optical system to illuminate the generated speckle patterns on a specimen; and a fluorescence imaging optical system to detect fluorescent emission from the fluorophores excited by the speckle illumination, by passing the radiated speckle patterns and fluorescence emission sequentially through at least one excitation filter and at least one emission filter, respectively The speckle pattern generator may generate the speckle illumination patterns, using either at least one reflection diffuser or at least one transmission diffuser or at least one spatial light modulator.

The speckle pattern generator may generate the speckle illumination patterns at least one color using at least one coherent source with at least one wavelengths.

The illumination optical system may include either diffraction limited far-field optics in transmission or reflection type or a near-field optics such as total internal reflection (TIR) optics.

The at least one excitation filter may excite fluorophores using the at least one color speckle patterns, and the at least one emission filter may selectively pass fluorescent emission lights in at least one color from the fluorophores.

At least one of the illumination optical system and the fluorescent image optical system may be disposed in a structure of at least one of a reflection microscope, a transmission microscope, and a near-field optical microscope.

The nano-scale resolution microscopy system may further include an image reconstruction algorithm to restore the images at high resolution using a set of sequentially measured fluorescence emission images using time dependent dynamic speckle illumination.

The image reconstruction algorithm may calculate data covariance matrices using the set of sequentially measured fluorescence emission images using time dependent dynamic speckle illumination.

The image reconstruction algorithm may obtain high resolution images by exploiting that the temporal profiles of fluorescence emission for adjacent fluorescence emissions are statistically uncorrelated due to the incoherence of speckle illumination.

The image reconstruction algorithm may decompose the data covariance matrix into the signal subspace and the noise subspace, and may reconstruct positions of fluorophores by exploiting the orthogonality of a model signal calculated from a fluorophore location with respect to the noise subspace.

The image reconstruction algorithm may reconstruct positions of fluorophores by exploiting that a model signal calculated from a fluorophore location is highly correlated with the signal subspace.

According to another aspect of the present invention, there is provided a method of obtaining an image using a nano-scale resolution microscopy system, the method including: at least one coherent sources in at least one color for the purpose of imaging fluorophores attached to a specimen; generating speckle illumination patterns by passing a light generated from at least one coherent sources in at least one color through at least one diffuser or spatial light modulator; radiating the generated speckle patterns to be exposed on a specimen, using at least one optical lens; and obtaining fluorescence emission images excited by the speckle patterns in at least one color, using at least one excitation filter and at least one emission filter.

The generating may include generating the speckle patterns in at least one color having an irregular pattern, using either a reflection type diffuser or a transmission type diffuser or spatial light modulator.

The at least one optical lens may correspond to a far-field optics, or a near-field optics.

The at least one coherent source may include lasers or other coherent light sources in at least one color.

The at least one excitation filter may selectively excite fluorophores using the speckle patterns with at least one colors, and the at least one emission filter may selectively pass fluorescent emission from the speckle illumination through at least one excitation filters.

The method may further include: sequentially obtaining florescent emission images by the fluorescent image optical system; and reconstructing images at high resolution by exploiting the signal and noise subspace structures of a data covariance matrix.

The reconstruction of the image at high resolution may include: generating speckle illumination pattern in at least one color; sequentially obtaining the fluorescence emission images, calculating a data covariance matrix and decomposing them into the signal and the noise subspaces; restoring high resolution images by exploiting the signal and noise subspace structure of the data covariance matrix.

The reconstruction of the image in high resolution may include: decomposing the data covariance matrix into the signal subspace and the noise subspace; and restoring positions of the fluorophores by exploiting the orthogonality of a model signal calculated at a fluorophore location with respect to the classified noise subspace.

According to still another aspect of the present invention, there is provided a nano-scale resolution microscopy system, including: an incident optical system; a fluorescent image optical system; a speckle pattern generator to generate speckle patterns in at least one color by passing, through at least one diffuser or at least one spatial light modulator, a light emitted from at least one coherent source in at least one color to detect fluorescent emission images of a specimen; and an image reconstruction algorithm execution unit to execute an image reconstruction algorithm, wherein the incident optical system and the fluorescent image optical system may include at least one optical lens disposed in a structure of at least one of a reflection microscope, a transmission microscope, and a near-field optical microscope, and the image reconstruction algorithm execution unit may execute the image reconstruction algorithm, thereby sequentially obtaining fluorescence emission images by the fluorescent image optical system, and reconstructing the images at high resolution by exploiting the statistical properties of the fluorescence emission temporal profile at every pixel excited by the speckle illumination.

The image reconstruction algorithm execution unit may generate speckle patterns to excite fluorophores, may calculate a data covariance matrix using sequentially obtained fluorescence emission images from a specimen excited by the speckle illumination pattern, and may reconstruct images with respect to the fluorescent probes location of the specimen based on a result of the calculation.

EFFECT

According to embodiments of the present invention, an image with respect to fluorophores in a specimen at high resolution may be obtained by obtaining a super resolution image at a nanometer scale, using time dependent speckle illumination pattern and sensor array signal processing.

According to embodiments of the present invention, a high power laser beam for a non-linear optical transition in fluorophores may be unnecessary. Furthermore, a nano-scale resolution microscopy system of the present invention may use not only a switchable fluorescence probes but also other non-switchable fluorescent probes and fluorescent proteins.

According to embodiments of the present invention, a high resolution image beyond the diffraction limit of a fluorescence microscope, that may be useful for basic and applied scientific researches, may be easily implemented by modifying a conventional fluorescence microscope to have a dynamic speckle pattern illuminator and image reconstruction software.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

According to embodiments of the present invention, a nano-scale resolution microscopy system may include at least one coherent light source and at least one diffusor or spatial light modulator or anytime of speckle pattern generator. The nano-scale resolution microscopy system may illuminate randomized pattern such as speckle patterns generated at the diffuser to a specimen, by changing the characteristics of the diffuser, then multiple snapshots of speckle patterns can be dynamically generated on the specimen. The nano-scale resolution microscopy system may change an optical or electrical characteristic of the diffuser. In case of roughness diffuser, rotating or translating of diffuser may change optical characteristics which cause speckle patterns, and in case of spatial light modulators, different electrical signals may change different random patterns look like a speckle pattern. Also, the nano-scale resolution microscopy system may continuously obtain fluorescence signals excited by the illuminated speckle patterns. The fluorescence signals may be passed through a dichroic mirror (DM) and an emission filter, and may be measured by a camera.

Figure 1:
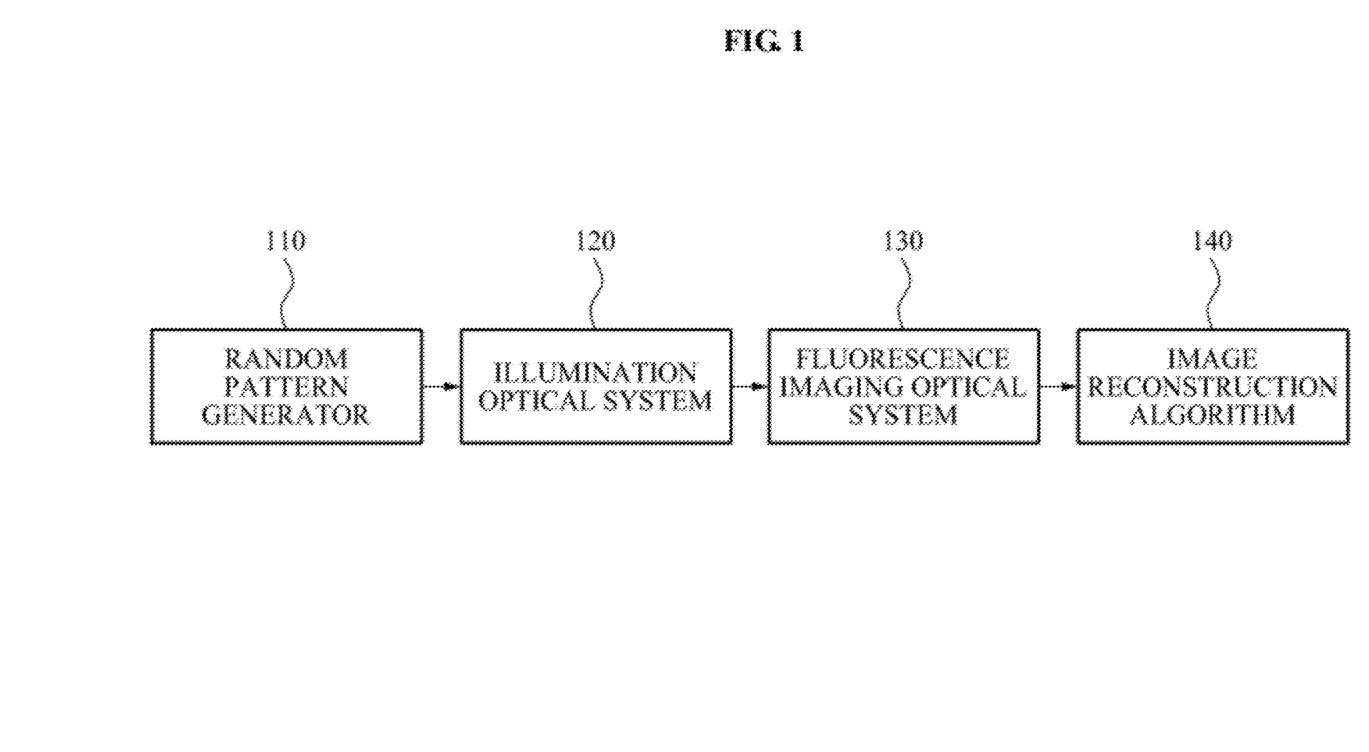
FIG. 1 is a diagram illustrating a structure of a nano-scale resolution microscopy system according to an embodiment of the present invention.

Thus, the nano-scale resolution microscopy system may include components as illustrated in FIG. 1. FIG. 1 is a diagram to describe a structure of a nano-scale resolution microscopy system according to an embodiment of the present invention.

Referring to FIG. 1, each component of the nano-scale resolution microscopy system may be shown in blocks.

The nano-scale resolution microscopy system may include a random pattern generator 110, an illumination optical system 120, a fluorescence imaging optical system 130, and an image reconstruction algorithm 140.

The random pattern generator 110 may include a diffuser and/or spatial light modulators. The random pattern generator 110 may generate speckle patterns by passing a light emitted from at least one coherent light source and random patterns by changing random patterns on modulator. The diffuser may scatter the light passed through the diffuser, and may output the light having a low spatial coherence with respect to adjacent regions. Instead of roughness diffuser, the spatial light modulators may be applied to generate random patterns by changing the electrical signal. The modulators may reflect or transmit the light from a continuous wave laser. The random pattern generator 110 may generate speckle patterns and random patterns having a low spatial coherence.

The illumination optical system 120 may illuminate the light passed through the diffuser to a specimen so that the speckle patterns generated by the random pattern generator 110 may be exposed on the specimen. Also, the illumination optical system 120 may overcome a diffraction limit of a fluorescence microscopy by disposing an optical lens where a size of an irregular pattern of the speckle patterns may have a diffraction limit, or by disposing a total internal reflection optical system to reduce the diffraction limit.

The fluorescence imaging optical system 130 may pass the speckle patterns illuminated by the illumination optical system 120, sequentially through at least one excitation filter and at least one emission filter. The fluorescence imaging optical system 130 may acquire a fluorescence signal by measuring a fluorescence emission signal excited by the illuminated speckle patterns.

Here, the at least one excitation filter may apply to excite a fluorophore by the speckle patterns illuminated from the illumination optical system 120, and the at least one emission filter may selectively pass fluorescence signals excited by the at least one excitation filter. Accordingly, the fluorescence signal excited by the speckle patterns may be selectively passed by the at least one emission filter after a fluorophore is excited by the at least one excitation filter.

The image reconstruction algorithm 140 may continuously obtain images measured by the fluorescence imaging optical system 130, and may reconstruct the images in nano-scale resolution by time dependent data that may change in every pixel, based on the continuously obtained images. In this instance, the data changed depending on time may be viewed more clearly in the reconstructed images, and fluorophores of a target object may be viewed in nano-scale resolution. The image reconstruction algorithm 140 may be executed by an image reconstruction algorithm execution unit.

The image reconstruction algorithm may exploit a characteristic of a temporal correlation between adjacent pixels being low in a spatial domain scattered by the diffuser.

Particularly, when a speckle pattern S generated by the diffuser is illuminated to a specimen, a mathematical model of images obtained by the fluorescence imaging optical system 130 may be given by:

$$I(x,y,;t)=\{PSF_{det}*[x_f(PSF_{ill}*s)]\}(x,y;t)+w(x,y;t). \quad \text{[Equation 1]}$$

Here, (x, y) denotes coordinates of a camera, t denotes time instances for each measurement, and S and $x_f$ denote a speckle pattern and fluorescence signals. Also, $PSF_{ill}$ denotes a point spread function of a condenser lens or an objective lens where the speckle pattern S may be convoluted, and $PSF_{det}$ denotes a point spread function of an objective lens where fluorescence signal may be convoluted.

Accordingly, the speckle pattern S generated according to Equation 1 may be convoluted with the point spread function of the condenser lens or the objective lens, and may be illuminated to the specimen, and the fluorescence signal $x_f$ emitted in response to the excitation light may be convoluted with the point spread function of the objective lens.

When Equation 1 is analytically expressed and point spread functions are expressed in a form of a single point spread function, Equation 2 may be derived.

$$I(x,y,;t)=x_f\iint PSF(x-x',y-y';t)s(x',y';t)dx'dy'+w(x,y;t). \quad \text{[Equation 2]}$$

Also, when Equation 2 is expressed as a matrix, and a point spread function that may be convoluted by Equation 2 is expressed as a convolution matrix A, Equation 3 may be derived.

$$\underline{I}(t)=A\underline{X}(t)+\underline{w}(t). \quad \text{[Equation 3]}$$

When a spatial covariance matrix R is calculated based on data I with respect to the changes of fluorescence signals, the structure may be given by:

$$R = \frac{1}{T}\int_0^T \underline{I}(t)\underline{I}^*(t)\,dt = APA^* + \sigma^2 I. \quad \text{[Equation 4]}$$

Here, T denotes a total amount of time consumed for obtaining images, I denotes data with respect to changes of fluorophores measured at a predetermined time, R denotes a spatial covariance matrix, $\sigma^2 I$ denotes a noise spatial covariance matrix, A denotes a point spread function of optical system, and P denotes a correlation of fluorophores.

Accordingly, based on the image reconstruction algorithm, the spatial covariance matrix may be calculated based on at least one of I the data with respect to changes of fluorophores signal measured at a predetermined time, R the spatial covariance matrix, $\sigma^2 I$ the noise spatial covariance matrix, A the point spread function of elements, and P the correlation of fluorescence probes.

We may express the spatial covariance matrix R, using the correlation P and the point spread function A of elements, and may express white noise w uncorrelated to the fluorescence signal.

A correlation between electromagnetic fields of a randomized speckle pattern may be given by:

$$P_{ij} = \frac{1}{T} \int x(\alpha_i, \beta_i; t) x^*(\alpha_i, \beta_i; t) \quad \text{[Equation 5]}$$

$$PSF_{ill}(\alpha_i, \beta_i) PSF_{ill}^*(\alpha_j, \beta_j) dt =$$

$$|x_f x_0|^2 e^{-\sigma_0^2 (1-\mu_0(\Delta\alpha, \Delta\beta))} R_{PSF}(\alpha, \beta)$$

Here, $\sigma^2_o$ denotes a phase change depending on a change in height of a surface of a diffuser, and $x_f$ and $x_o$ denote fluorescence signals and a randomized speckle pattern. Also, $\mu_o$ denotes a function with respect to a distance between two points, which may have a characteristic of converging to 1 when the distance between the two points becomes closer. $R_{PSF}$ is the illumination point spread function autocorrelation function.

Accordingly, when the change $\sigma^2_o$ in height of the surface of the diffuser becomes greater, a function of the correlation of speckle patterns between the pixel elements may converge to a delta function, and a matrix of the correlation P between the adjacent fluorophores may correspond to a near diagonal matrix. In illumination optical system, excitation pattern for fluorescence imaging is convolved with illumination point spread function. When the matrix of the correlation P between the adjacent fluorophores may be expressed as a diagonal matrix, a performance of an estimator that may reconstruct the fluorophore may be as good as a performance of an estimator that may reconstruct a single molecule.

Further, according to the sensor array signal processing perspective, positions of the fluorophores may be reconstructed using a subspace method which may find a position of a target signal by classifying a spatial covariance matrix R of a measurement data into a signal subspace and a noise subspace. In particular, we may use a Multiple Signal Classification (MUSIC) method as well as other various types of subspace methods.

The MUSIC method may correspond to a method generally used for an antenna sensor array signal processing perspective, which may use the covariance matrix decomposition by Equation 6.

$$R = APA^* + \sigma^2 I \quad \text{[Equation 6]}$$

$$= U\Sigma V^H$$

$$= [u_s \; u_n] \begin{bmatrix} \sigma_s + \sigma^2 & 0 \\ 0 & \sigma^2 \end{bmatrix} [v_s \; v_n]^H.$$

The MUSIC method may perform a singular value decomposition with respect to a spatial covariance matrix R, and may classify a singular vector U into a signal subspace $u_s$ and a noise subspace $u_n$ based on a size of a white noise distribution $\sigma^2$, from a distribution of singular values. Also, the MUSIC method may further use:

$$P_{MU} = \frac{1}{\|u_n^H A\|_p}. \quad \text{[Equation 7]}$$

Here, p corresponds to $0 \leq p \leq \infty$. According to the MUSIC method based on Equation 7, a null-spectrum of the noise subspace may be calculated based on the singular vector $u_n$ and the point spread function A with respect to the noise subspace, and a position of a signal may be reconstructed as the peak of the spectrum in Equation 7. According to the method, the positions of the fluorophores of the target object may be reconstructed by classifying a signal of the measured images into a signal subspace and a noise subspace, and based on a principle of a target signal existing in a position where noise generated by the classified noise subspace may be minimized.

Figure 2:
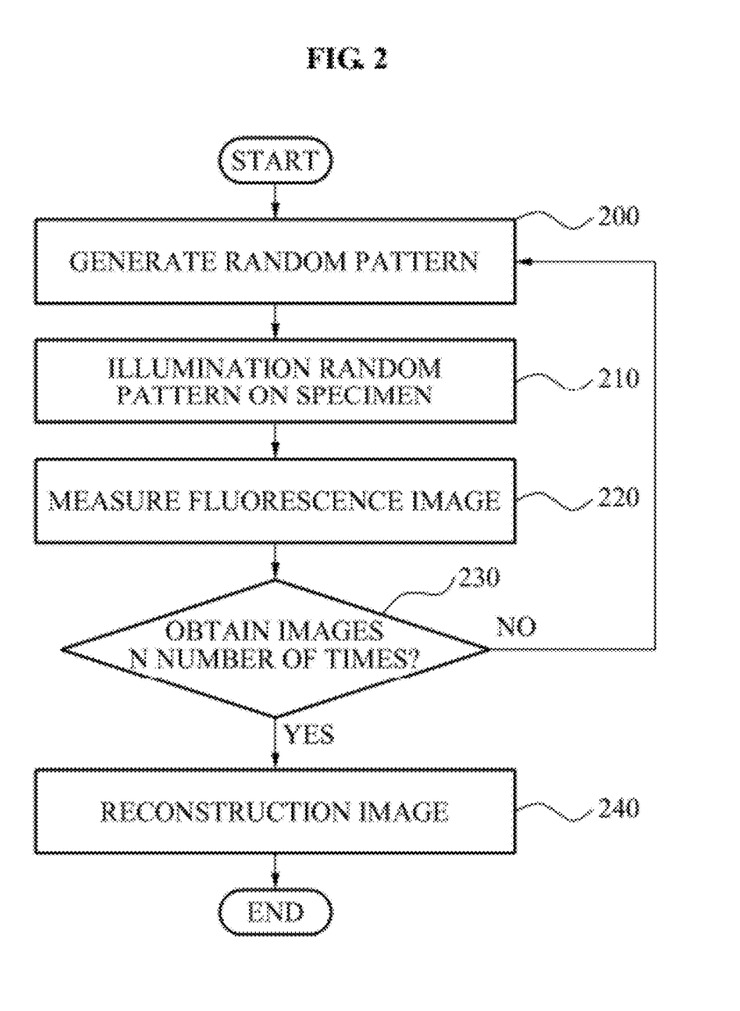
FIG. 2 is a diagram illustrating operations of the nano-scale resolution microscopy system illustrated in FIG. 1.
Figure 3A:
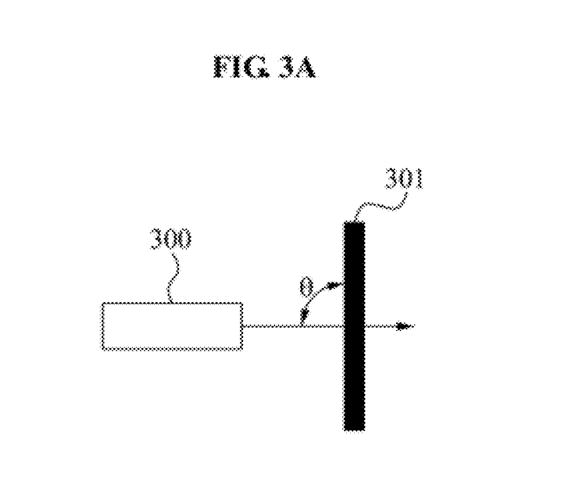
FIGS. 3A and 3B are diagrams illustrating coherent lights passing through a transmission diffuser or a reflection diffuser in the nano-scale resolution microscopy system.
Figure 3B:
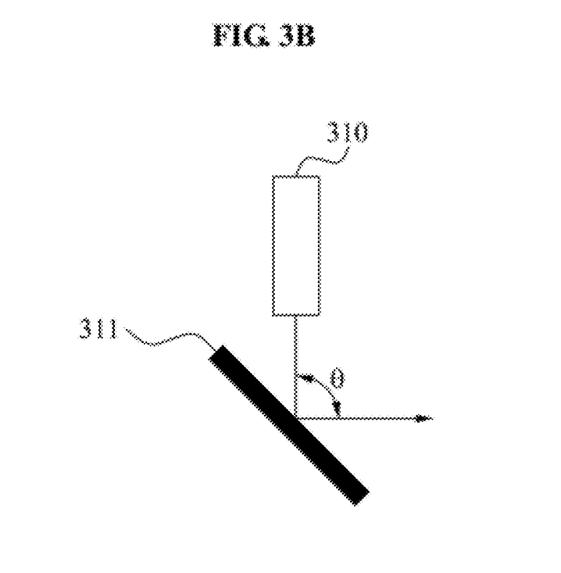

FIG. 2 illustrates operations of the nano-scale resolution microscopy system illustrated in FIG. 1, and FIGS. 3A and 3B illustrate coherent lights 300 and 310 passing through diffusers 301 and 311 in the nano-scale resolution microscopy system. Particularly, the diffuser 301 of FIG. 3A may correspond to a transmission diffuser, and the diffuser 311 of FIG. 3B may correspond to a reflection diffuser.

When light is emitted from a continuous wave laser in order to measure fluorescence signal of a target object, the random pattern generator 110 may generate speckle patterns by passing or transmitting the light emanated from the laser through a diffuser, in operation 200.

Particularly referring to FIG. 3A, the coherent light 300 of the light emitted from the continuous wave laser may be passed through the transmission diffuser 301.

When the coherent light 300 is passed through the transmission diffuser 301, the speckle patterns may be generated. When the transmission diffuser 301 diffuses and passes the coherent light 300, the coherent light 300 passed through the transmission diffuser 301 may have incoherence according to a change in mechanical, optical, or electrical characteristics.

Referring to FIG. 3B, the coherent light 310 may be reflected from the reflection diffuser 311. When the reflection diffuser 311 diffuses and reflects the coherent light 310, the coherent light 310 reflected from the reflection diffuser 311 may have incoherence according to a change in mechanical, optical, or electrical characteristics.

Consequently, the transmission diffuser 301 or the reflection diffuser 311 may continuously generate speckle patterns of the temporal coherent lights 300 and 310.

In operation 210, the illumination optical system 120 may illuminate the speckle patterns, generated in operation 200, to be illuminated on a specimen using at least one optical component.

In operation 220, the fluorescence imaging optical system 130 may excite fluorophores by passing the illuminated speckle patterns through at least one excitation filter. The fluorescence imaging optical system 130 may pass a fluorescence signal generated as a result of the excitation, through at least one emission filter. The fluorescence imaging optical system 130 may measure the fluorescence signal excited by the speckle patterns. The measured image may have fluorescence signals.

In operation 230, the fluorescence imaging optical system 130 may continuously obtain images, N number of times.

In operation 240, the image reconstruction algorithm 140 may reconstruct the images in nano-scale resolution by multiple measurement data dependent on time that may change in every pixel, based on the continuously obtained images. As aforementioned, the image reconstruction algorithm 140 may use a sensor array signal processing algorithm such MUSIC scheme.

The illumination optical system 120 and the fluorescence imaging optical system 130 may dispose the at least one optical component in a structure of at least one of a reflection microscope, a transmission microscope, and a TIR optical microscope.

Figure 4:
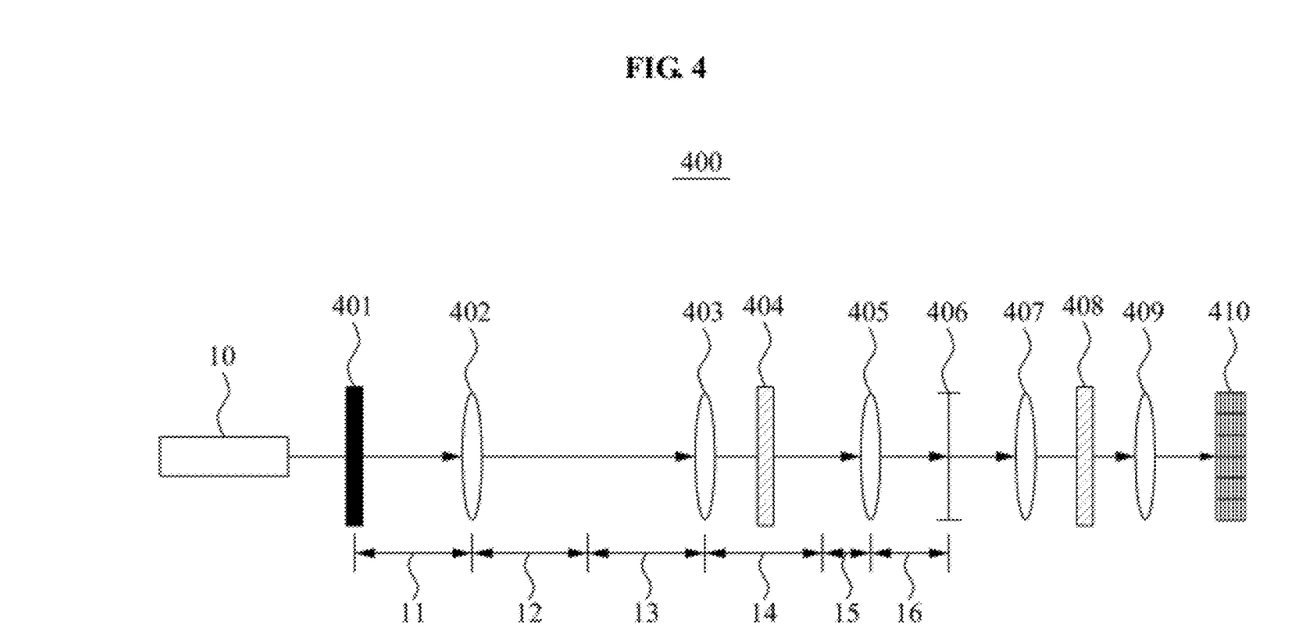
FIG. 4 is a diagram illustrating an example of a microscope structure that may be utilized in the nano-scale resolution microscopy system of FIG. 1.

FIG. 4 is a diagram illustrating an example of a microscope structure that may be utilized in the nano-scale resolution microscopy system of FIG. 1.

Referring to FIG. 4, the example may represent a structure of the fluorescence imaging optical system 130 corresponding to a transmission microscope 400.

In the transmission microscope 400, a coherent light 10 may be passed through a transmission diffuser 401, and then speckle patterns may be generated by the transmission diffuser 401.

The transmission microscope 400 may include the transmission diffuser 401, a first optical lens 402, a second optical lens 403, an excitation filter 404, a condenser lens 405, a specimen 406, an objective lens 407, an emission filter 408, an adapter lens 409, and a charge-coupled device (CCD)/complementary metal oxide semiconductor (CMOS) camera 410.

Particularly, the transmission microscope 400 may arrange the first optical lens 402, the second optical lens 403, and the condenser lens 405 in a row so that the generated speckle patterns may be located in a back focal length 11 of the first optical lens 402, a back focal length 13 of the second optical lens 403 may correspond to a front focal length 12 of the first optical lens 402, and a front focal length 14 of the second optical lens 403 may correspond to a back focal length 15 of the condenser lens 405.

Also, the transmission microscope 400 may dispose the excitation filter 404, which may filter a light wavelength to excite a fluorescence probe, between the second optical lens 403 and the condenser lens 405.

Accordingly, the speckle patterns may be finally illuminated to be exposed on the specimen 406, and an image of the light emitted as a result of the excitation of the fluorophores passed through the excitation filter 404 may be magnified by the objective lens 407, and may be passed through the emission filter 408. The light may be selectively passed by the emission filter 408, and may correspond to a fluorescence signal which is a part of the light passed though the emission filter 408. The image of the light passed through the emission filter 408 may be exposed on the CCD/CMOS camera 410 by the adapter lens 409.

Figure 5:
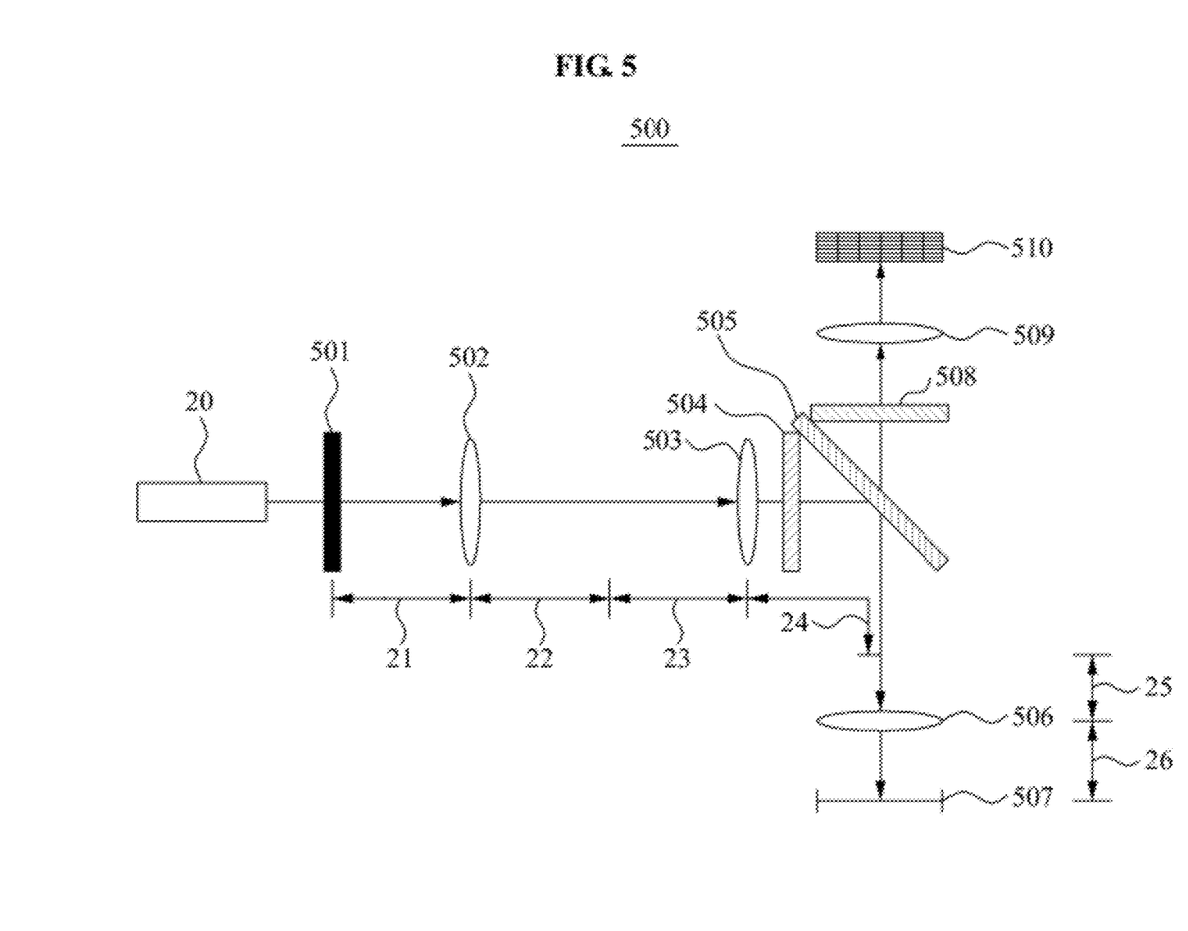
FIG. 5 is a diagram illustrating another example of a microscope structure that may be utilized in the nano-scale resolution microscopy system of FIG. 1.

FIG. 5 is a diagram illustrating another example of a microscope structure that may be realized in the nano-scale resolution microscopy system of FIG. 1.

Referring to FIG. 5, the example may represent a structure of the fluorescence imaging optical system 130 corresponding to a reflection microscope 500.

Similar to the transmission microscope 400, the reflection microscope 500 may arrange a transmission diffuser 501, a first optical lens 502, a second optical lens 503, an objective lens 505, and a specimen 506 in a row so that a back focal length 23 of the second optical lens 503 may correspond to a front focal length 22 of the first optical lens 502, and a front focal length 24 of the second optical lens 503 may correspond to a back focal length 25 of the objective lens 505.

The reflection microscope 500 may dispose an excitation filter 504, and a dichroic filter 507 between the second optical lens 503 and the objective lens 505, and may also dispose an emission filter 508, an adapter lens 509, and a CCD/CMOS camera 510 in a path where a light may be transmitted from the dichroic filter 507.

Accordingly, a coherent light 20 may be passed through the transmission diffuser 501, and speckle patterns may be generated by the transmission diffuser 501. Then, the generated speckle patterns may be illuminated through the first optical lens 502, the second optical lens 503, and the objective lens 505 to be exposed on the specimen 506. A light emitted from excited fluorophores may be magnified by the objective lens 505, transmitted from the dichroic filter 507, and passed through the emission filter 508. The light passed through the emission filter 508 may be selectively passed through by the emission filter 508, and may correspond to a fluorescence signal which is a part of the light passed though the emission filter 408. The image of the light passed through the emission filter 508 may be exposed on the CCD/CMOS camera 510 by the adapter lens 509.

Figure 6:
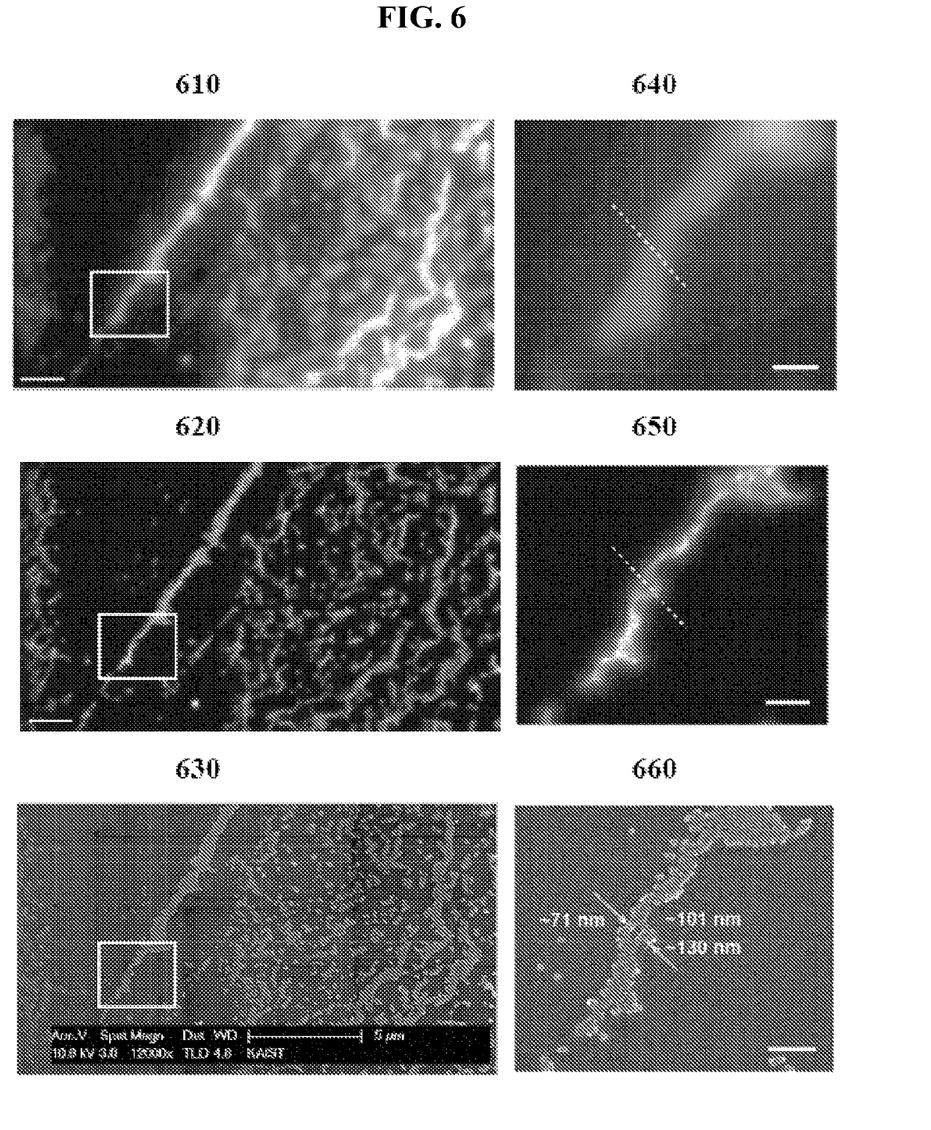
FIG. 6 is a diagram illustrating an example of images resulting from randomly aggregated fluorescence nano-particles measured by the nano-scale resolution microscopy system illustrated in FIG. 1.
Figure 7:
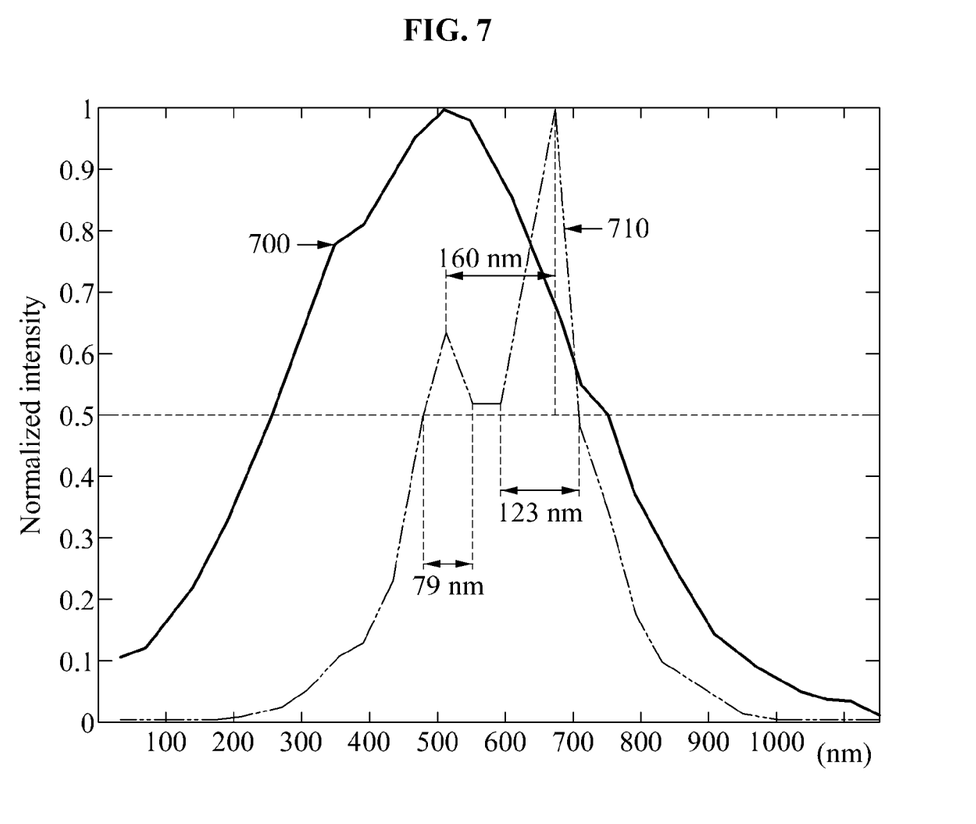
FIG. 7 is a profile of reconstructed images illustrating a comparison of the images resulting from fluorescence nano-particles illustrated in FIG. 6.

FIG. 6 is a diagram illustrating an example of resulting images of randomly aggregated fluorescence nano-particles performed by the nano-scale resolution microscopy system illustrated in FIG. 1, and FIG. 7 is a graph to compare the resulting images of fluorescence nano-particles illustrated in FIG. 6.

Referring to FIG. 6, the reconstructed large field-of-view of randomly aggregated 50 nm nanoparticles is presented. The conventional microscope images in 610 and 640 are observed using a 100× magnification oil-immersion objective lens. Images 620 and 650 are reconstructed images, and images 630 and 660 are scanning electron microscope (SEM) images to confirm the reconstruction images by present invention. There exists an empty space surrounded by nanoparticles in white boxes in images 610, 620, and 630. Images 640, 650, and 660 are the white boxes images of 610, 620, and 630, respectively. As can be seen from the dashed lines in 640 and 650, the width of the empty space is ~100 nm and the widths of other two fluorophores are 70 nm and 130 nm represented in 660. As illustrated in an image 650, present invention resolved the empty space as well as the 70 nm fluorophore probe, whereas the space is not revealed in a conventional microscope image 640. Based on the nanoparticle experimental results, present invention achieved 70 nm lateral resolution and 3-fold resolution improvement over the diffraction limit ($\lambda_{em}/2NA_{oil}$) where $NA_{oil}$ and $\lambda_{em}$ are about 1.3 and 570 nm, respectively.

When comparing image data 700 around a dashed line of the image 640 and image data 710 around a dashed line of the image 650, the graph illustrated in FIG. 7 may be represented.

Referring to FIG. 7, the horizontal axis of the graph may correspond to a length of an actual sample, and the vertical axis of the graph may correspond to a size of a normalized signal. The image data 710 around the dashed line of the image 650 may have reduced background noise and improved resolution when compared to the image data 700 of the dashed line of the image 640.

Figure 8:
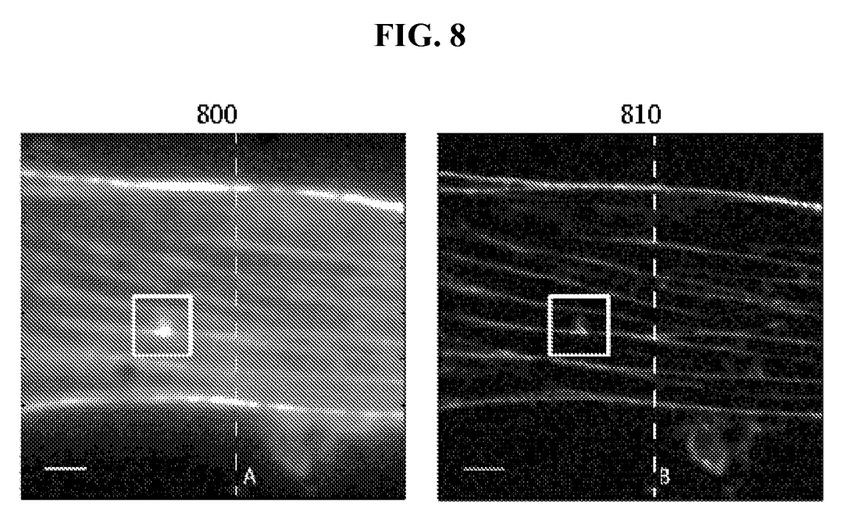
FIG. 8 is a diagram illustrating an example of images resulting from fluorescence stained actin with respect to the nano-scale resolution microscopy system illustrated in FIG. 1, and a conventional microscopy system.
Figure 9:
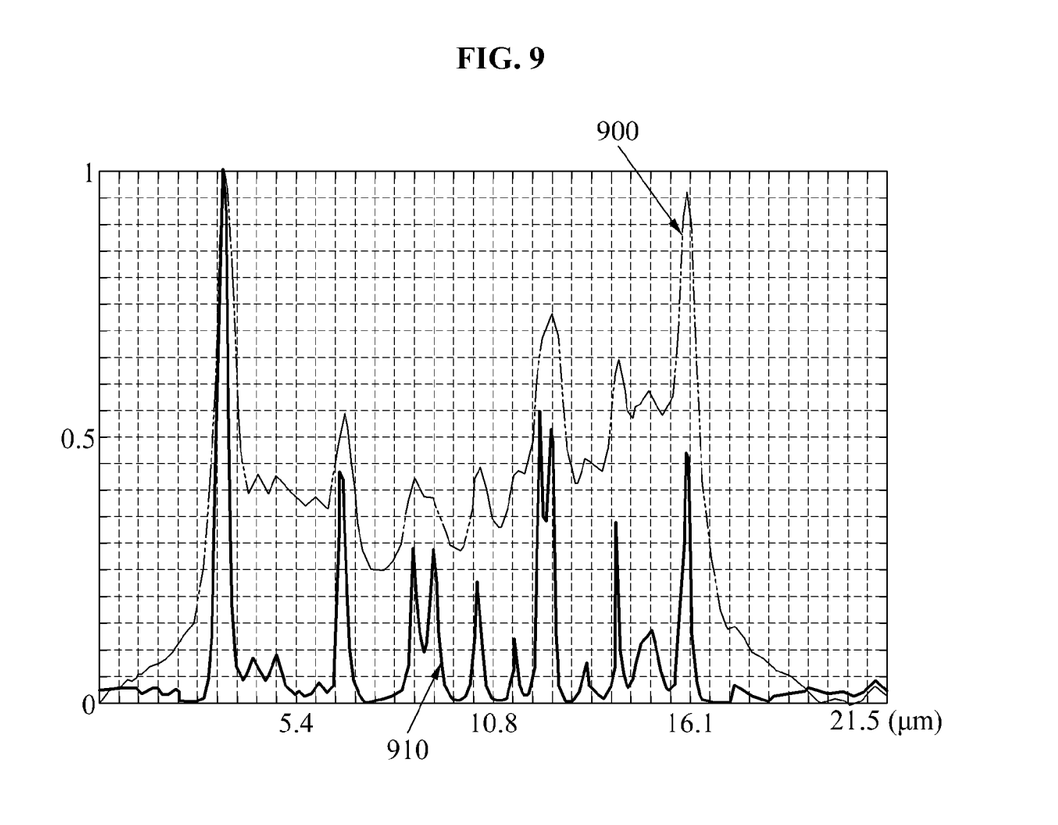
FIG. 9 is a profile of reconstructed images illustrating a comparison of the images resulting from fluorescence stained actin illustrated in FIG. 8.

FIG. 8 is a diagram to describe an example of images resulting from actin stained by fluorescence dye with respect to the nano-scale resolution microscopy system illustrated in FIG. 1, and a conventional microscopy system, and FIG. 9 is a graph to compare the resulting images of actin stained by fluorescence dye illustrated in FIG. 8.

Referring to FIG. 8, the resulting images of actin stained by fluorescence dye may correspond to images observed using a 60× magnification objective lens, by staining of actin in a cell. Particularly, an image 800 may correspond to an image of the cell observed using a conventional fluorescence microscope, and an image 810 may correspond to an image of the cell reconstructed using the nano-scale resolution microscopy system according to embodiments of the present invention.

When comparing image data 900 around a dotted line A of the image 800 and image data 910 around a dotted line B of the image 810, the graph illustrated in FIG. 9 may be represented.

Referring to FIG. 9, the horizontal axis of the graph may correspond to a length of an actual sample, and the vertical axis of the graph may correspond to a size of a normalized signal. The image data 910 around the dotted line B of the image 810 may have reduced background noise and improved resolution when compared to the image data 900 of the dotted line A of the image 800.

Figure 10A:
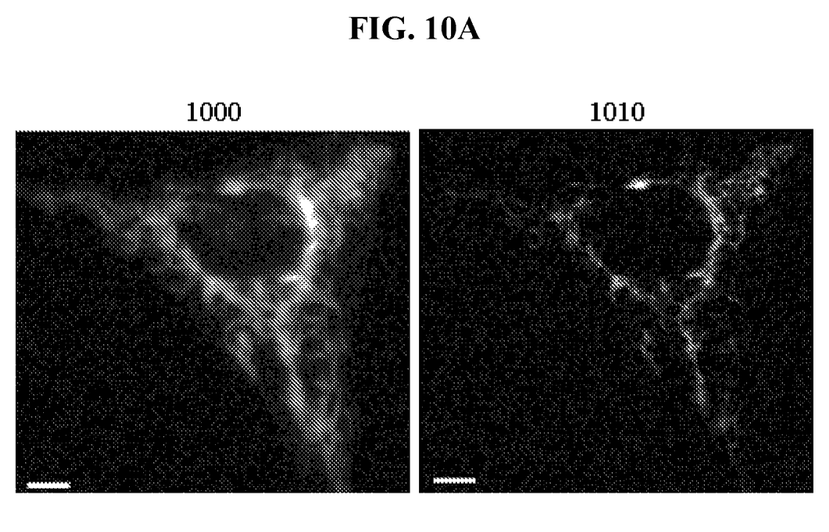
FIGS. 10A and 10B are diagrams illustrating examples of images resulting from fluorescence stained mitochondria by the nano-scale resolution microscopy system illustrated in FIG. 1.
Figure 10B:
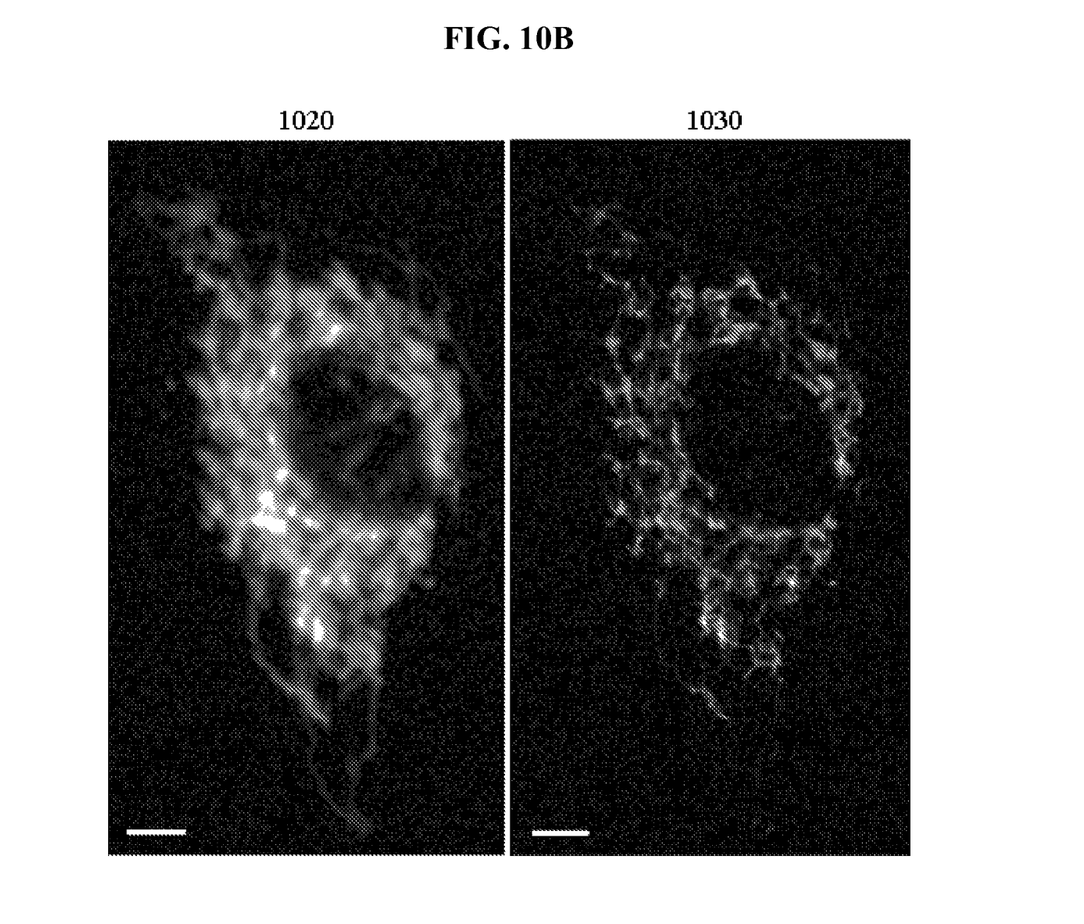

FIGS. 10A and 10B are diagrams illustrating examples of images resulting from fluorescence stained mitochondria by the nano-scale resolution microscopy system illustrated in FIG. 1.

Referring to FIGS. 10A and 10B, the images resulting from stained mitochondria may correspond to images observed using a 60× magnification objective lens, by fluorescence stained mitochondria in a cell. In particular, images 1000 and 1020 may correspond to images of the cell observed using a conventional fluorescence microscopy, and images 1010 and 1030 may correspond to images of the cell observed using the nano-scale resolution microscopy system according to embodiments of the present invention. The images 1010 and 1030 observed using the nano-scale resolution microscopy system according to embodiments of the present invention may show clearer images when compared to the images 1000 and 1020 observed using the conventional fluorescence microscopy, and accordingly improvement in resolution may be observed.

The above-described exemplary embodiments of the present invention may be recorded in computer-readable media including program instructions to implement various operations embodied by a computer. The media may also include, alone or in combination with the program instructions, data files, data structures, and the like. The media and program instructions may be those specially designed and constructed, or they may be of the kind well-known and available to those having skill in the computer software arts.

Embodiments of the present invention have provided us with new insight into current state-of-the-art nanoscopy techniques, and what performance they can achieve. For example, PALM and STORM satisfy the condition of diagonal signal covariance matrix due to the non-overlapping photo-switching fluorophores, so the sensor arrays signal processing theory guarantees that its fundamental performance limitation approaches that of single molecular target detection. A similar explanation can be given if the quantum-dot blinking statistics are totally uncorrelated. As discussed before, these approaches, however, require a new type of fluorophores to make the signal covariance matrix diagonal. Unlike these microscopy, present invention does not require photoswitchable dye because the signal source can be made to be uncorrelated by using the spatial incoherence of speckle illumination.

Present invention may be implemented by simply modifying a conventional epi-fluorescence optical microscopy such that a rotating diffuser and low power continuous wave laser can be used. To demonstrate the improved resolution of present invention, we imaged phantom and biological samples. The phantom image results clearly revealed that the resolution of present invention can achieve over the diffraction limit. The stained actin and mitochondria imaged by present invention reveals ultra-structures that were not visible using conventional fluorescence.

The resolution limiting effect of illumination optics can be further reduced by employing total internal reflection fluorescence (TIRF) optics, as was done in PALM and STORM. Furthermore, the proposed nanoscale image reconstruction algorithm can be combined with PALM and STORM to improve the resolution furthermore.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A nano-scale resolution fluorescence microscopy system, comprising:
    a speckle pattern generator configured to generate speckle patterns by passing, through a diffuser, a light emitted from at least one coherent light source in at least one color to detect fluorescent emission in at least one color from fluorophores attached to a specimen;
    an illumination optical system to radiate the generated speckle patterns to be exposed on a specimen, by disposing at least one optical lens; and
    a fluorescent image optical system configured to detect fluorescence emission images of the specimen excited by the speckle patterns in at least one color, by passing the radiated speckle patterns sequentially through at least one excitation filter and detecting the emission images through at least one emission filter; and
    an image reconstruction algorithm configured to sequentially obtain fluorescent emission images by the fluorescent image optical system, and to reconstruct the image at high resolution by detecting temporal profile of fluorescence emission data at every pixel, based on the sequentially obtained images,
    wherein the image reconstruction algorithm is configured to process fluorescence emission images obtained sequentially based on any type of array signal processing algorithms that uses data covariance matrix by calculating the spatial correlation matrix between pixels, and reconstruct images with respect to the fluorophores using the signal and noise subspace structure of the data covariance matrix.

2. The nano-scale resolution microscopy system of claim 1, wherein the speckle pattern generator is configured to generate the speckle patterns, using either at least one reflection diffuser or transmission diffuser or any type of spatial light modulator.

3. The nano-scale resolution microscopy system of claim 1, wherein the incident optical system comprises either transmission type or reflection type microscope optics in a far-field or near field optical system.

4. The nano-scale resolution microscopy system of claim 1, wherein
the at least one excitation filter is configured to excite fluorephores in at least one color using the speckle patterns in at least one color, and
the at least one emission filter selectively passes fluorescent emission light in at least one color from the fluorephores excited by the speckle patterns in at least one color through the at least one excitation filter.

5. The nano-scale resolution microscopy system of claim 1, wherein at least one of the incident optical system and the fluorescent image optical system is disposed in a structure of at least one of a reflection microscope or a transmission microscope in a far-field or near-field optics.

6. The nano-scale resolution microscopy system of claim 1, wherein the image reconstruction algorithm is configured to process fluorescence emission images obtained sequentially based on any type of signal processing algorithms.

7. The nano-scale resolution microscopy system of claim 1, wherein the image reconstruction algorithm is configured to process fluorescence emission images obtained sequentially based on an sensor array signal processing algorithms, calculate a data covariance matrix by calculating the spatial correlation matrix between pixels, and reconstruct images with respect to the fluorophores using any statistical signal processing and optimization algorithm.

8. The nano-scale resolution microscopy system of claim 1, wherein the image reconstruction algorithm is configured to calculate the data covariance matrix by calculating the spatial correlation matrix between pixels and taking the temporal average of the correlation matrix.

9. The nano-scale resolution microscopy system of claim 1, wherein the image reconstruction algorithm is configured to reconstruct the image by exploiting a characteristic of a temporal correlation of the fluorescence emission temporal profiles being small between adjacent fluorophores.

10. The nano-scale resolution microscopy system of claim 1, wherein the image reconstruction algorithm is configured to reconstruct the image by exploiting a characteristic of incoherence of the speckle illumination.

11. The nano-scale resolution microscopy system of claim 1, wherein the image reconstruction algorithm is configured to decompose a data covariance matrix into the signal and the noise subspaces, and reconstruct positions of the fluorephores of the target object by exploiting the orthogonality of a model signal calculated from a fluorophore location with respect to the noise subspace.

12. The nano-scale resolution microscopy system of claim 1, wherein the image reconstruction algorithm is configured to decompose a data covariance matrix into the signal and the noise subspaces, and reconstruct positions of the fluorephores of the target object by exploiting that a model signal calculated from a fluorophore location is highly correlated with the signal subspace.

13. A nano-scale resolution fluorescence microscopy, comprising:
a speckle pattern generator configured to generate speckle patterns by passing, through a diffuser, a light emitted from at least one coherent light source in at least one color to detect fluorescent emission in at least one color from fluorophores attached to a specimen;
an illumination optical system configured to radiate the generated speckle patterns to be exposed on a specimen, by disposing at least one optical lens;
a fluorescent image optical system configured to detect fluorescence emission images of the specimen excited by the speckle patterns in at least one color, by passing the radiated speckle patterns sequentially through at least one excitation filter and detecting the emission images through at least one emission filter; and
an image reconstruction algorithm configured to sequentially obtain fluorescent emission images by the fluorescent image optical system, and to reconstruct the image at high resolution by detecting temporal profile of fluorescence emission data at every pixel, based on the sequentially obtained images,
wherein the image reconstruction algorithm reconstruct positions of the fluorephores of the target object by exploiting that the measurement data is highly correlated with the numerically calculated forward model.

14. A method of obtaining an image using a nano-scale resolution microscopy system, the method comprising:
illuminating coherent light from at least one coherent source to image fluorophores in specimen;
generating speckle patterns by passing the light emitted from the coherent through a diffuser;
radiating the generated speckle patterns to be exposed on a specimen, using at least one optical lens;
photographing a fluorescent light of the speckle patterns, by passing the radiated speckle patterns sequentially through at least one excitation filter and at least one emission filter;
continuously obtaining images photographed by the fluorescent image optical system; and
restoring the images in high resolution by sensing time dependent data that changes in every pixel, based on the continuously obtained images,
wherein the restoring of the image in high resolution comprises:
decomposing a data covariance matrix into the signal and the noise subspaces, and
reconstructing positions of the fluorephores of the target object by exploiting the orthogonality of a model signal calculated from a fluorophore location with respect to the noise subspace.

15. The method of claim 14, wherein the generating comprises generating the speckle patterns having an irregular pattern, using either a reflection diffuser or a transmission diffuser or any type of spatial light modulator.

16. The method of claim 14, wherein the at least one optical lens corresponds to an optical lens where a size of an irregular pattern of the speckle patterns has a diffraction limit, or a total internal reflection optical system to reduce the diffraction limit.

17. The method of claim 14, wherein
the at least one excitation filter excites a fluorephores of the speckle patterns, and
the at least one emission filter selectively passes a fluorescent emission from the light excited by the at least one excitation filter.

18. The method of claim 14, wherein the restoring of the image in high resolution comprises:
processing fluorescence emission images obtained sequentially based on an sensor array signal processing algorithms,
calculating a data covariance matrix by calculating the spatial correlation matrix between pixels, and reconstructing images with respect to the fluorophores using any statistical signal processing and optimization algorithm.

19. A method of obtaining an image using a nano-scale resolution microscopy system, the method comprising:
illuminating coherent light from at least one coherent source to image fluorophores in specimen;

generating speckle patterns by passing the light emitted from the coherent through a diffuser;

radiating the generated speckle patterns to be exposed on a specimen, using at least one optical lens;

photographing a fluorescent light of the speckle patterns, by passing the radiated speckle patterns sequentially through at least one excitation filter and at least one emission filter;

continuously obtaining images photographed by the fluorescent image optical system; and restoring the images in high resolution by sensing time dependent data that changes in every pixel, based on the continuously obtained images, wherein the restoring of the image in high resolution comprises:

decomposing a data covariance matrix into the signal and the noise subspaces, and reconstructing positions of the fluorophores of the target object by exploiting that a model signal calculated from a fluorophore location is highly correlated with the signal subspace.

20. A nano-scale resolution fluorescence microscopy system, comprising:

a speckle pattern generator configured to generate speckle patterns by passing, through a diffuser, a light emitted from at least one coherent light source in at least one color to detect fluorescent emission in at least one color from fluorophores attached to a specimen;

an illumination optical system configured to radiate the generated speckle patterns to be exposed on a specimen, by disposing at least one optical lens;

a fluorescent image optical system configured to detect fluorescence emission images of the specimen excited by the speckle patterns in at least one color, by passing the radiated speckle patterns sequentially through at least one excitation filter and detecting the emission images through at least one emission filter; and an image reconstruction algorithm configured to sequentially obtain fluorescent emission images by the fluorescent image optical system, and to reconstruct the image at high resolution by detecting temporal profile of fluorescence emission data at every pixel, based on the sequentially obtained images, wherein the image reconstruction algorithm is configured to decompose the data covariance matrix into the signal and the noise subspaces, and reconstruct positions of the fluorephores of the target object by exploiting that the signal subspace is highly correlated with the numerically calculated forward model.

* * * * *